US007744590B2

(12) United States Patent
Eells et al.

(10) Patent No.: US 7,744,590 B2
(45) Date of Patent: *Jun. 29, 2010

(54) RED TO NEAR-INFRARED PHOTOBIOMODULATION TREATMENT OF THE VISUAL SYSTEM IN VISUAL SYSTEM DISEASE OR INJURY

(75) Inventors: Janis T. Eells, Madison, WI (US); Margaret T. T. Wong-Riley, Brookfield, WI (US); Harry T. Whelan, Whitefish Bay, WI (US)

(73) Assignee: Medical College of Wisconsin Research Foundation, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/056,458

(22) Filed: Mar. 27, 2008

(65) Prior Publication Data

US 2009/0062888 A1   Mar. 5, 2009

Related U.S. Application Data

(63) Continuation of application No. 10/758,793, filed on Jan. 16, 2004, now Pat. No. 7,354,432.

(60) Provisional application No. 60/440,816, filed on Jan. 17, 2003.

(51) Int. Cl.
*A61B 18/18* (2006.01)

(52) U.S. Cl. ............................. 606/4; 606/6; 128/898; 607/88; 607/89

(58) Field of Classification Search ...................... None
See application file for complete search history.

(56) References Cited

U.S. PATENT DOCUMENTS

| 3,930,504 | A | * | 1/1976 | de Laforcade | ................. | 606/4 |
| 5,279,298 | A | * | 1/1994 | Flower | ....................... | 600/321 |
| 5,511,563 | A | * | 4/1996 | Diamond | ..................... | 128/898 |
| 6,676,655 | B2 | | 1/2004 | McDaniel | | |
| 2003/0099596 | A1 | * | 5/2003 | North et al. | .................. | 424/9.4 |

OTHER PUBLICATIONS

Rosner et al., "Dose and Temporal Parameters in Delaying Injured Optic Nerve Degeneration by Low-energy Laser Irradiation", 1993, Lasers in Surgery and Medicine, 13(6), 611-7.*

* cited by examiner

*Primary Examiner*—Henry M Johnson, III
*Assistant Examiner*—Lynsey Crandall
(74) *Attorney, Agent, or Firm*—Quarles & Brady LLP

(57) ABSTRACT

A method of treating visual system disease is disclosed. One embodiment comprises the steps of (a) exposing a component of a patient's visual system to light treatment, wherein the light treatment is characterized by wavelength of between 630-1000 nm and power intensity between 10-90 mW/cm$^2$ for a time of 1-3 minutes, and (b) observing restoration of visual system function.

19 Claims, 12 Drawing Sheets

A.

A

RED TO NEAR-INFRARED PHOTOBIOMODULATION TREATMENT OF THE VISUAL SYSTEM IN VISUAL SYSTEM DISEASE OR INJURY

CROSS-REFERENCE TO RELATED APPLICATION

This application is a continuation application of U.S. patent application Ser. No. 10/758,793, filed on Jan. 16, 2004, now U.S. Pat. No. 7,354,432 which claims the benefit of U.S. provisional application Ser. No. 60/440,816, filed Jan. 17, 2003. Both U.S. patent application Ser. No. 10/758,793 and U.S. provisional application Ser. No. 60/440,816 are hereby incorporated by reference herein.

STATEMENT REGARDING FEDERALLY SPONSORED RESEARCH OR DEVELOPMENT

This invention was made with United States government support awarded by the following agencies: Defense Advanced Research Projects Agency Grant DARPA N66001-01-1-8969 and N66001-03-1-8906, National Institute of Environmental Health Sciences Grant ES06648, National Eye Institute Core Grant P30-EY01931, National Eye Institute Grants EY11396 and EY05439. The United States has certain rights in this invention.

BACKGROUND OF THE INVENTION

Decrements in mitochondrial function have been postulated to be involved in the pathogenesis of numerous retinal and optic nerve diseases, including age-related macular degeneration, diabetic retinopathy, and Leber's hereditary optic neuropathy (J. F. Rizzo, *Neurology* 45:11-16, 1995; M. J. Baron, et al., *Invest. Ophthalmol. Visual Sci.* 42:3016-3022, 2001; V. Carelli, et al., *Neurochem. Int.* 40:573-584, 2002). Decrements in mitochondrial function have also been postulated to be involved in the pathogenesis in methanol intoxication (M. M. Hayreh, et al., *Neurotoxicity of the Visual System*, eds. Merigan, W. & Weiss, B. (Raven, New York), pp. 35-53, 1980; G. Martin-Amat, et al., *Arch. Ophthalmol.* 95:1847-1850, 1977; M. T. Seme, et al., *J. Pharmacol. Exp. Ther.* 289:361-370, 1999; M. T. Seme, et al., *Invest. Ophthalmol. Visual Sci.* 42:834-841, 2001). Methanol intoxication produces toxic injury to the retina and optic nerve, frequently resulting in blindness. A toxic exposure to methanol typically results in the development of formic academia, metabolic acidosis, visual toxicity, coma, and, in extreme cases, death (J. T. Eells, *Browning's Toxicity and Metabolism of Industrial Solvents: Alcohols and Esters*, eds. Thurman, T. G. Kaufmann, F. C. (Elsevier, Amsterdam), Vol. IV, pp. 3-15, 1992; R. Kavet and K. Nauss, *Crit. Rev. Toxicol.* 21:21-50, 1990). Visual disturbances generally develop between 18 and 48 hours after methanol ingestion and range from misty or blurred vision to complete blindness. Both acute and chronic methanol exposure have been shown to produce retinal dysfunction and optic nerve damage clinically (J. T. Eells, supra, 1992; R. Kavet and K. Nauss, supra, 1990; J. Sharpe, et al., *Neurology* 32:1093-1100, 1982) and in experimental animal models (S. O. Ingemansson, *Acta Ophthalmol.* 158 (Supp): 5-12, 1983; J. T. Eells, et al., *Neurotoxicology* 21:321-330, 2000; T. G. Murray, et al., *Arch. Ophthalmol.* 109:1012-1016, 1991; E. W. Lee, et al., *Toxicol. Appl. Pharmacol.* 128:199-206, 1994).

Formic acid is the toxic metabolite responsible for the retinal and optic nerve toxicity produced in methanol intoxication (M. M. Hayreh, et al., supra, 1980; G. Martin-Amat, et al., supra 1977; M. T. Seme, et al., supra, 1999; M. T. Seme, supra, 2001; G. Martin-Amat, et al., *Toxicol. Appl. Pharmacol.* 45:201-208, 1978). Formic acid is a mitochondrial toxin that inhibits cytochrome c oxidase, the terminal enzyme of the mitochondrial electron transport chain of all eukaryotes (P. Nicholls, *Biochem. Biophys. Res. Commun.* 67:610-616, 1975; P. Nicholls, *Biochim. Biophys. Acta* 430:13-29, 1976). Cytochrome oxidase is an important energy-generating enzyme critical for the proper functioning of almost all cells, especially those of highly oxidative organs, including the retina and brain (M. T. T. Wong-Riley, *Trends Neurosci.* 12:94-101, 1989). Previous studies in our laboratory have established a rodent model of methanol-induced visual toxicity and documented formate-induced mitochondrial dysfunction and retinal photoreceptor toxicity in this animal model (M. T. Seme, et al., supra, 1999; M. T. Seme, et al., supra, 2001; J. T. Eells, et al., supra, 2000; T. G. Murray, et al., supra, 1991).

Photobiomodulation by light in the red to near-IR range (630-1,000 nm) using low-energy lasers or light-emitting diode (LED) arrays has been shown to accelerate wound healing, improve recovery from ischemic injury in the heart, and attenuate degeneration in the injured optic nerve (H. T. Whelan, et al., *J. Clin. Laser Med. Surg.* 19:305-314, 2001; U. Oron, et al., *Lasers Sur. Med.* 28:204-211, 2001; E. M. Assa, et al., *Brain Res.* 476:205-212, 1989; M. J. Conlan, et al., *J. Clin. Periodont.* 23:492-496, 1996; W. Yu, et al., *Lasers Surg. Med.* 20:56-63, 1997; A. P. Sommer, et al., *J. Clin. Laser Med. Surg.* 19:27-33, 2001). At the cellular level, photoirradiation at low fluences can generate significant biological effects, including cellular proliferation, collagen synthesis, and the release of growth factors from cells (M. J. Conlan, et al., supra, 1996; T. Karu, *J. Photochem. Photobiol.* 49:1-17, 1999; M. C. P. Leung, et al., *Lasers Surg. Med.* 31:283-288, 2002). Our previous studies have demonstrated that LED photoirradiation at 670 nm (4 J/cm$^2$) stimulates cellular proliferation in cultured cells and significantly improves wound healing in genetically diabetic mice (H. T. Whelan, et al., supra, 2001; A. P. Sommer, et al., supra, 2001). Despite its widespread clinical application, the mechanisms responsible for the beneficial actions of photobiomodulation have not been elucidated. Mitochondrial cytochromes have been postulated as photoacceptors for red to near-IR light energy and reactive oxygen species have been advanced as potential mediators of the biological effects of this light (Karu, supra, 1999; N. Grossman, et al., *Lasers Surg. Med.* 22:212-218, 1998).

BRIEF SUMMARY OF THE INVENTION

In one embodiment, the present invention is a method of treating disease or injury of the visual system, comprising the steps of (a) exposing a component of a patient's visual system to light treatment, wherein the light treatment is characterized by wavelength between 630-1000 nm and power intensity between 10-90 mW/cm$^2$ for a time of 1-3 minutes, and (b) observing restoration or protection of visual system function. Preferably, the wavelength is selected from the group consisting of 670 nm, 830 nm and 880 nm.

In one embodiment of the invention, the light treatment is characterized by an energy density of between 0.5-20 J/cm$^2$. In a preferred embodiment, the energy density is between 2-10 J/cm$^2$.

Preferably, the patient is exposed to light treatment multiple times and is exposed to light treatment intervals of 24 hours.

In a preferred form of the invention, the component of the visual system comprises the patient's retina or is selected from the group consisting of cornea and optic nerve.

Other features, objects or advantages of the present invention will become apparent to one of skill in the art after examination of the specification, claims and drawings.

BRIEF DESCRIPTION OF THE SEVERAL VIEWS OF THE DRAWINGS

FIG. 6(A-B) is a set of graphs.

FIG. 7A is a set of micrographs of a laser grid at 15 minutes and 1 month post-laser treatment in both LED-treated and non-LED-treated tissue.

FIG. 8A is a set of micrographs of lateral geniculate nuclei of monkeys with monocular central retinal laser injury both treated and not treated with NIR-LED.

FIG. 9 is a graph of the multifocal ERG response in nanovolts versus pre-laser, post-laser, four day post-laser and eleven day post-laser treatment for LED-treated and non-treated tissue.

DETAILED DESCRIPTION OF THE INVENTION

Low energy photon irradiation by light in the far red to near infrared spectral range (630-1000 nm) using low energy lasers or light emitting diode arrays has been found to modulate various biological processes in cell culture and animal models [(M. J. Conlan, et al., *J. Clin. Periodont.* 23:492-496, 1996; W. Yu, et al., *Lasers Surg. Med.* 20:56-63, 1997; A. P. Sommer, et al., *J. Clin. Laser Med. Surg.* 19:27-33, 2001; T. Karu, *J. Photochem. Photobiol.* 49:1-17, 1999)]. As described above, this phenomenon of photobiomodulation has been applied clinically in the treatment soft tissue injuries and to accelerate wound healing [(H. T. Whelan, et al., *J. Clin. Laser Med. Surg.* 19:305-314, 2001; U. Oron, et al., *Lasers Surg. Med.* 28:204-211, 2001; E. M. Assa, et al., *Brain Res.* 476:205-212, 1989; M. J. Conlan, et al., supra, 1996)]. The mechanism of photobiomodulation by red to near infrared light at the cellular level has been ascribed to the activation of mitochondrial respiratory chain components resulting in initiation of a signaling cascade which promotes cellular proliferation and cytoprotection.

Figure 1:
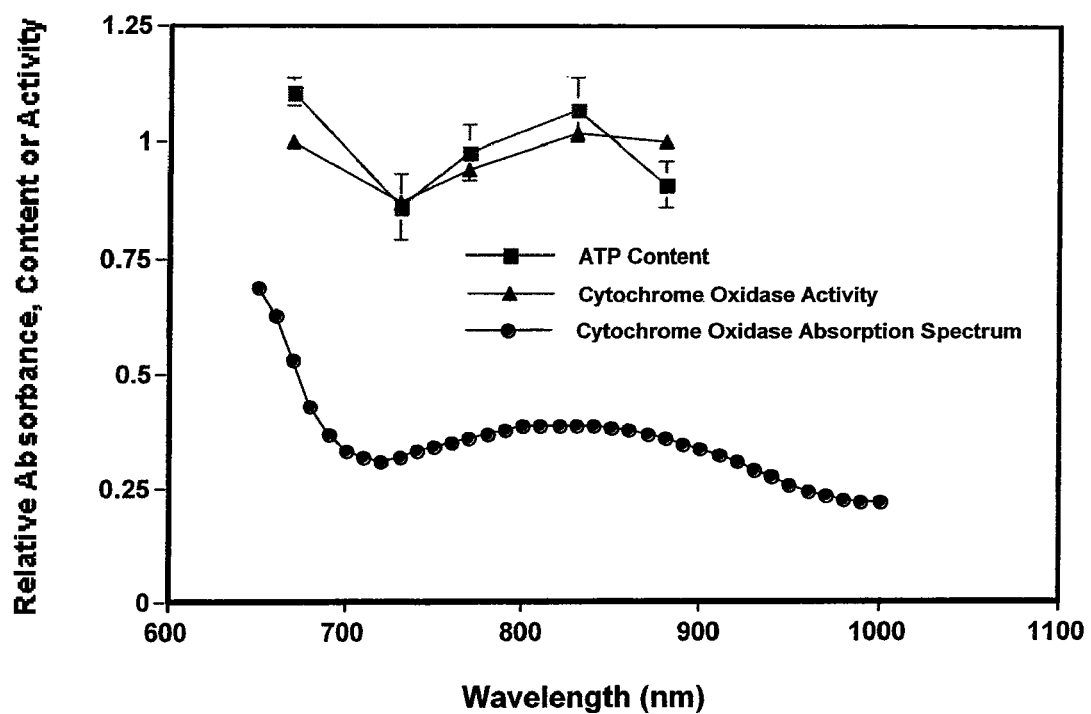
FIG. 1 is a graph of wavelength versus relative absorbance, content or activity.

The therapeutic effects of red to near infrared light may result, in part, from the stimulation of cellular events associated with increases in cytochrome c oxidase activity. In support of this theory, we have demonstrated in primary neuronal cells that LED photobiomodulation (670 nm at 4 $J/cm^2$) reverses the reduction in cytochrome oxidase activity produced by the blockade of voltage-dependent sodium channel function by tetrodotoxin (M. T. T. Wong-Riley, et al., NeurReport 12:3033-3037, 2001). In addition, we have shown that the action spectrum for LED stimuation of cytochrome oxidase activity and cellular ATP content parallels the absorption spectrum for cytochrome oxidase. (FIG. 1). The structured nature of the action spectrum is strong evidence that cytochrome oxidase is a primary photoacceptor molecule for light in the far red to near infrared region of the spectrum. Our recent work has provided evidence for the therapeutic benefit of photobiomodulation in the survival and functional recovery of the retina and optic nerve in vivo after acute injury by the mitochondrial toxin, formic acid generated in the course of methanol intoxication. (Eells, et al., *Proc. Natl. Acad. Sci.* 100(6):3439-3441, incorporated by reference herein.) In addition, we have provided data below indicating that 670 nm LED treatment promotes retinal healing and improved visual function following high intensity laser-induced retinal injury in adult non-human primates.

These findings provide a link between the actions of red to near infrared light on mitochondrial oxidative metabolism in vitro and ocular injury in vivo. Importantly, the results of these studies and others suggested to us that photobiomodulation with red to near infrared light augments recovery pathways promoting neuronal viability and restoring neuronal function following ocular injury. There was no evidence of damage to the retina or optic nerve following 670 nm LED treatment. Based on these findings, we suggest that photobiomodulation represents a non-invasive and innovative therapeutic approach for the treatment of ocular injury and acute and chronic ocular disease.

In one broad aspect, the present invention is a method of treating ocular disease comprising the steps of exposing a component of a patient's visual system to light treatment wherein the light treatment is characterized by wavelength between 630-1000 nm and power intensity between 25-50 $mW/cm^2$ for a time of 1-3 minutes (equivalent to an energy density of 2-10 $J/cm^2$) and observing restoration or protection of visual function. The sections below further describe and characterize the present invention.

Suitable LED

In a preferred form of the present invention, the therapeutic photobiomodulation is a achieved using an light emitting diode as the source of red to near infrared light unlike the prior art which utilized light generated by low energy laser. Lasers have limitations in beam width, wavelength capabilities, and size of the injury or tissue that can be treated. In addition, heat generated from laser light can damage biological tissue, and the concentrated beam of laser light may accidentally damage the eye. Light-emitting diode (LED) arrays were developed for the National Aeronautics and Space Administration manned space flight experiments. In comparison with lasers, LED technology generates negligible amounts of heat, is clinically proven to be safe, and has achieved non-significant risk status for human trials by the U.S. Food and Drug Administration.

Preferably, the present inventions utilizes a noncoherent light source capable of irradiating the entire retina and optic system with monochromatic light in the far-red to near-infrared region of the spectrum. An example of a commercially available, preferable LED source is the ISO 9001 LED (QUANTUM SPECTRALIFE) array obtainable from Quantum Devices (Barneveld, Wis.).

Light in the far-red to near infrared region of the spectrum is known to penetrate nearly 20 cm into irradiated tissue. A preferable device is composed of a monolithic array of hybrid GaAlAs light emitting diodes designed to emit diffused monochromatic light. Preferable LED chips have been fabricated to emit specific peak wavelengths (between 650-940 nm) of photon energy and the system has been designed to deliver high intensity light energy to an isolated area of exposure without heat.

Preferably, the LEDs are shielded by a glass barrier and are unlensed, allowing for even dispersion of light over a 1800 viewing angle allowing each LED chip to act as a point source offering a high degree of illumination uniformity. The surface energy (photon flux or power intensity) delivered by the LED units is between 25-50 mW/cm$^2$. LED units that we have worked with produce monochromatic light at wavelengths in the far red (670 nm) to near infrared (700-900 nm) region of the spectrum. The LED arrays can be custom fabricated from GaAlAs (galinium aluminum arsinate) diodes to produce light with peak wavelengths between 650 nm and 940 nm. The devices that we have employed have peak wavelengths of 670, 728, 830 and 880 nm with bandwidths of 25-35 nm at 50% power. LED units and low energy lasers could be constructed that emit at other peak wavelengths in the range of 630-1000 nm.

Peak wavelengths of 670 nm, 830 nm, and 880 nm with bandwidths of 25-30 nm have been used with success in experimental and clinical studies. Both benchtop LED units (bandwidth 25-30 cm at 50% power) with 8×10 cm rectangular arrays and portable NIR-LED units with 5 cm diameter circular arrays obtained from Quantum Devices, Inc. (Barneveld, Wis.) have been used in our experimental and clinical studies. In our experimental and clinical studies of NIR-LED treatment of ocular injury or disease, 670 nm LED irradiation was administered at a power intensity between 25-50 mW/cm$^2$ between 1-3 minutes to produce an energy density of 4 J/cm$^2$.

In a preferred embodiment of the present invention, 670 nm LED irradiation administered at a power intensity between 25-50 mW/cm$^2$ between 1-3 minutes produces an energy density of 4 J/cm$^2$ and promotes retinal healing and improves visual function. It is likely that other NIR wavelengths (830, 880 nm) will also promote retinal healing and protect against retinal injury, but we have no animal model evidence for this at this time.

The LED unit is typically positioned at a distance of approximately 2.5 cm from the eye in each case. We envision that one would wish to position the light source at between 0.5 cm and 4.0 cm from the eye or 0.5-1.0 cm from the top, side or back of the head for irradiation of other components (optic nerve, lateral geniculate nucleus, superior colliuculus, etc.) of the visual system. As described below, the position from the target factors into the entire energy density calculation.

Optimal Treatment Protocols

There are four important treatment parameters variables in the therapy of the present invention: (1) Energy density or fluence, (2) light wavelength (3) number of treatments and (4) the treatment interval.

(1) Energy density or fluence is the product of LED power intensity and duration of irradiation and is expressed as Joules per square centimeter (J/cm$^2$). For effective NIR-light therapy of the present invention, the energy density cannot be too low, otherwise there will be no biological effect. Energy density should also not be too great or it might produce adverse effects. Prior studies have suggested that biostimulation occurs at energy densities between 0.5 and 20 J/cm$^2$, whereas energy densities above 20 J/cm$^2$ exert bioinihibitory effects. Preferable energy density of the present invention is between 0.5-20 J/cm$^2$, most preferably between 2-10 J/cm$^2$. This range is based on evidence which documents that exposure to near-infrared light at energy densities (fluence) between 2-10 J/cm$^2$ promotes cellular energy metabolism, cell division and wound healing, protects against toxin-induced retinal damage and promotes healing and improved visual function following high intensity laser-induced retinal injury.

(2) With respect to LED wavelength, the majority of our studies have been conducted using 670 nm LED light and there is substantial evidence that NIR-LED treatment at 670 nm is beneficial for the treatment of ocular toxicity, retinal laser injury and retinal disease. NIR-LED light at wavelengths corresponding to the absorption peaks of the copper centers in the cytochrome oxidase molecule (670 nm, 830 nm and 880 nm) have been shown to be effective in promoting the recovery of cytochrome oxidase activity and energy metabolism in cultured primary neurons. These three wavelengths are preferable wavelengths in the present invention. (M. Wong-Riley, et al., EPEC Conference, European Bioenergetics Conference, 2002)

Band width can vary depending on technology and type of light source used. Although LED arrays are preferred in the present invention, the invention includes any far-red to near infrared light source (low energy lasers and LED arrays) which can produce energy densities between 0.5-20 J/cm$^2$. Preferable bandwidth for low energy laser light sources would be 4 nm and preferable band width for LEDs would be 25-50 nm. The entire preferred range would be 4-50 nm.

(3) In acute ocular injury situations, the optimal time for initial NIR-LED treatment should be within 24 hours of injury, if possible, based on our studies of acute ocular injury in rodent and primate models. However, if treatment is not feasible within the first 24 hours, it should be initiated as soon as possible. Molecular studies document upregulation of genes encoding energy producing and antioxidant proteins within 24 hours of NIR-LED treatment.

In summary, a preferred form of the present invention uses near infrared wavelengths of 630-1000, most preferably, 670-900 nm (bandwidth of 25-35 nm) with an energy density exposure of 0.5-20 J/cm$^2$, most preferably 2-10 J/cm$^2$, to produce photobiomodulation. This is accomplished by applying a target dose of 10-90, preferably 25-50 mW/cm$^2$ LED generated light for the time required to produce that energy density. Time requirements are calculated as: Power-intensity (mW/cm$^2$)×Time (seconds)÷1,000=Energy Density (J/cm$^2$).

(4) Treatment intervals of 24 hours have been shown to be beneficial for ocular injuries. Other studies have documented efficacy with treatments administered 2-3 times per day. It is likely that treatment spaced 2-3 days apart may also be effective. For chronic diseases, NIR-LED treatments administered at weekly intervals may be beneficial.

We suggest a treatment regime as described below, at 5, 25 and 50 hours. We suggest that the treatment be within 1-3 minutes of duration to provide the appropriate energy density.

(5) Number of treatments: We have demonstrated success in treatment of acute ocular injuries with as few as 2, preferably 3 or more, treatments and as many as 21 treatments administered at 1 day intervals. For the treatment of chronic diseases, NIR-LED treatments may be administered indefinitely.

Suitable Treatment Methods

In a preferred embodiment of the present invention, one would expose any component of a patient's visual system to the therapeutic effects of the light treatment described above. By "visual system" we mean to include the cornea, iris, lens, retina, optic nerve, optic chiasm, lateral geniculate nucleus, superior colliculus, pretectal nucleic, the accessory optic system, the oculomotor system, pulvinar, optic radiations, visual cortex, and associational visual cortical areas.

Exposure of the visual system may occur by treating with light directed into the eyes, thus irradiating the cornea, lens, iris, retina and optic nerve head. Alternatively, the device can be oriented so that the light is directed through the back of the head, thus irradiating the visual cortex or through the sides or top of the head thus irradiating the other components of the visual system.

One would wish to observe restoration or protection of visual function as measured in any conventional way that assesses visual function.

Therapeutic endpoints for treatment of corneal abrasion would include absence of fluorescein staining of the cornea. For retinal injury or disease, therapeutic endpoint measurement would include: (1) Fundoscopy or fundus photography which is an assessment of the appearance of the fundus or back of the eye, (note that the retina and optic nerve are observed by using special lenses); (2) Optical coherence tomography which measures the thickness (cross sectional architecture) of the retina; (3) Flash, flicker or multifocal electroretinogram recordings which measure the electrical response of the rod and cone photoreceptors in the retina to a light stimulus; (4) The visual evoked cortical potentials which access the integrity of the retino-geniculo striate pathway by measuring the electrical response of the visual area of the brain recorded from scalp electrodes to color vision testing; and (5) Visual acuity assessment using optotype (Snellen-style) eye charts. One would expect to see improvement or protection of the retina as measured by the methods described above.

For the optic nerve, therapeutic endpoint measurement would include the measurement of the visual evoked cortical potential from regions of the LGN or superior colliculus, to which the optic nerves project and the Pupillary Light Reflex test, which tests the integrity of the optic nerve (cranial nerve 2) and the oculomotor nerve (cranial nerve 3).

Therapeutic endpoints for improvement of visual function (measuring LED improvement of disease or injury to other components of the visual system—optic nerve, LGN visual pathways, etc.) preferably involves the use of a battery of tests which serve as standardized assessments for evaluation of the visual functions important in ensuring that visual perceptual processing is accurately completed. These include assessment of visual acuity (distant and reading), contrast sensitivity function, visual field, oculomotor function visual attention and scanning.

More detailed descriptions of retinal and visual function tests include:

1. Kinetic (Goldmann) perimetry ("Perimetry" is the quantitative testing of the side vision).

2. Automated (computerized) perimetry. In this test, spots of light are automatically projected into predetermined areas of the visual field. The test continues until the dimmest light is found that can be seen in each area of the side vision. These visual field tests provide important information.

3. Critical Flicker Fusion Frequency (CFF). Patients view a flickering light to test the ability of the optic nerve to conduct impulses with uniform speed. This test has proven to be very useful in identifying visual loss due to optic nerve damage.

4. Infra-red video pupillography. This is a way of seeing the pupils clearly in the dark so that a more certain diagnosis can be made. We also use it to transilluminate the iris to identify local iris causes for pupillary abnormalities.

5. Electroretinography. A regular ERG (eletroretinogram) records the electrical activity of the whole retina in response to light and helps to tell us if the rods and cones of the retina are firing in the correct way.

6. The Multi-focal ERG (MERG) does about a hundred ERGs at once by illuminating various little bits of the retina sequentially. It uses a computer to sort out the dizzying torrent of information and then it presents a map of the sensitivity of various parts of the retina, based on the electrical activity (in response to light) of all those different regions. If this map matches the map from perimetry, then the problem is in the retina and not in the optic nerve or brain.

7. Multi-focal Visual-Evoked Potentials (MVEP). Using a MERG stimulus, information can be picked up from the scalp that tells us if the visual pathways in the brain are damaged.

8. Computer controlled infra-red sensitive pupillography. This method is used to monitor pupillary movements in response to different types of light in order to quantify how much damage there might be in the visual system.

9. Computer controlled "Pupil" Perimetry. This method uses the pupil movement in response to small lights presented in the field of vision as an objective indicator of how well the eye sees the light.

10. Computer recording of eye movements. This instrument can be used for monitoring pupil movements—but it also has the capacity to record the small movements of both eyes at the same time to see if they are tracking together and have normal movements in different directions of gaze.

11. Optical Coherence Tomography (OCT). This is a new device that looks at the retina at the back of the eye and measures the thickness of the layer of nerves coming from all quadrants of the retina and leading into the optic nerve. This nerve fiber layer may be thickened, thinned or normal, depending on the nature of the disease affecting the optic nerve.

12. Ishihara Color Vision Test Cards. Used for color vision evaluation. A test chart on color dots that appear as identifiable numbers or patterns to individuals who have various types of color vision deficits.

The retina is a complex sensory organ composed of different cell types arranged in distinct layers. The term "retinal function" will be used to refer to (1) activation of these layers by a light stimulus and (2) the processes required for maintenance of the cell. Different diseases may affect the retinal layers or cell types in a selective fashion. Congenital stationary night blindness affects transmission of visual signals in the rod-mediated visual pathway whereas achromatopsia affects only the cone pathway. Other diseases may affect both photoreceptor types in a defined location on the retina. Examples are the macular dystrophies, such as Stargardt's and age-related macular degeneration. Other diseases, such as glaucoma or optic neuropathy appear to affect primarily the ganglion cells, located on the surface of the inner retina.

Assessment of the efficacy of a therapeutic intervention in one of these retinal diseases therefore depends on the specific disorder. Congenital stationary nightblindness would be best assessed by the full-field electroretinogram in a patient that has been adapted to darkness for about 30 minutes. Conversely achromatopsia, absent cone function, is best assessed by a full-field electroretinogram under light-adapted conditions and with a rapidly flickering flash stimulus that isolates cone function. Diseases of the macula are evident in the multifocal ERG, but not the full-field. This is due to the fact the macula, with several hundred thousand photoreceptors makes a very small contribution to the full-field ERG signal, which is the sum of 12 million or more photoreceptors. For this reason, assessment of the therapeutic efficacy of an intervention to treat Stargardt's disease or age-related macular degeneration, would be best accomplished by the multifocal ERG. Neither full-field ERGs nor multifocal ERGs contain a significant contribution from the ganglion cell layer. Assessment of interventions to affect the progression of glaucoma or Leber's hereditary optic neuropathy thus use the visually-evoked cortical potential because the visual cortical response is wholly-dependent on ganglion cell function and because the ERG is not affected in these diseases.

The summary, there are a number of different tests used in clinical ophthalmology that are designed to objectively measure the function of the retina. The retina must perform a number of jobs in order to convert a quantum of light entering the eye into an action potential in the visual cortex. The activation of the retinal layers by light results in the generation of electric fields in various levels of the visual system that can be recorded non-invasively. In theory, the NIR therapy could be beneficial in a wide range of diseases since it appears to affect basic cellular responses to insult such as ATP production and apoptosis. Thus there would be no one test that would be appropriate to assessing all the diseases that might benefit for NIR therapy.

For further assessment information, one may wish to consult American Optometric Association (AOA), Comprehensive adult eye and vision examination: Reference Guide for Clinicians. St. Louis (Mo.): American Optometric Association (AOA); 1994; Clinical Ophthalmology: *A Systematic Approach* by Jack J. Kanski, et al., Butterworth-Heinemann Medical; 5th edition (Jun. 2, 2003fe); *A Textbook of Clinical Ophthalmology*, 2nd Edition; and *A Practical Guide to Disorders of the Eyes and Their Management* by Ronald Pitts Crick (King's College Hospital, London) and Peng Tee Khaw (Moorfields Eye Hospital, London); and *Noninvasive Diagnostic Techniques in Ophthalmology* Barry R. Masters (Editor), ISBN: 0387969926, Pub. Date: August 1990 Publisher: Springer-Verlag New York, Incorporated.

Treatment Candidates

Numerous ocular diseases and injuries are likely to benefit from NIR-LED therapy. These include: 1) Acute ocular injuries to the cornea, retina and optic nerve, such as corneal abrasions, acute retinal ischemia, retinal detachment, light or laser induced retinal injuries. 2) Intoxications affecting the visual system following exposure to, or ingestion of, environmental toxins (e.g. methanol, pesticides) and drugs (e.g. ethambutal). 3) Chronic retinal and optic nerve diseases including, but not limited to, glaucoma, age-related macular degeneration, diabetic retinopathy, Leber's hereditary optic neuropathy, and other mitochondrial diseases with ocular manifestations. 4) Retinopathies and optic neuropathies resulting from nutritional deficiencies (e.g. folate, vitamin $B_{12}$). 5) Lesions of any centers in the visual system, including the optic nerve, optic chiasm, optic radiation, dorsal lateral geniculate nucleus, superior colliculus, and the visual cortex. Lesions could be induced by accident, trauma, hemorrhage, blood clot, ischemia, tumor, inflammation, infection or genetic defects.

EXAMPLES

Example 1

Led Treatment Protects the Rat Retina from Histopathic Changes Induced by Methanol-Derived Formate In General We hypothesize that the therapeutic effects of red to near-IR light result, in part, from the stimulation of cellular events associated with increases in cytochrome c oxidase activity. In support of this hypothesis, we have recently demonstrated in primary neuronal cells that LED photobiomodulation (670 nm at 4 $J/cm^2$) reverses the reduction in cytochrome oxidase activity produced by the blockade of voltage-dependent sodium channel function by tetrodotoxin (M. T. T. Wong-Riley, et al., *NeuroReport* 12:3033-3037, 2001). The present studies extended these investigations to an in vivo system to determine whether 670-nm LED treatment would improve retinal function in an animal model of methanol-induced mitochondrial dysfunction.

Using the electroretinogram (ERG) as a sensitive indicator of retinal function, we demonstrated that three brief (2 minutes, 24 seconds) 670-nm LED treatments 4 $J/cm^2$) delivered 5, 25, and 50 hours after the initial dose of methanol attenuated the retinotoxic effects of methanol-derived formate. Our studies demonstrate a significant recovery of rod- and M-cone mediated retinal function as well as a significant recovery of UV-cone mediated function in LED-treated rats. We further show that LED treatment protected the retina from methanol-induced histopathology. The present study provides evidence that 670 nm LED treatment promotes the recovery of retinal function and protects the retina against the cytotoxic actions of the mitochondrial toxin, formic acid. Our findings are consistent with hypothesis that LED photobiomodulation at 670 nm improves mitochondrial respiratory chain function and promotes cellular survival in vivo. They also suggest that photobiomodulation may enhance recovery from retinal injury and from other ocular diseases in which mitochondrial dysfunction is postulated to play a role.

Methods

Materials. LED arrays (8×10 cm) were obtained from Quantum Devices (Barneveld, Wis.). Methanol (HPLC grade) obtained from Sigma was diluted in sterile saline and administered as a 25% (wt/vol) solution. Thiobutabarbitol sodium salt (Inactin) was purchased from Research Biochemicals (Natick, Mass.). Atrpine sulfate was obtained from AmVet Pharmaceuticals (Fort Collins, Colo.). Hydroxypropyl methylcellulose (2.5%) drops were acquired from IOLAB Pharmaceuticals, Claremont, Calif. Atropine sulfate ophthalmic solution drops were purchased from Phoenix Pharmaceutical (St. Joseph, Mo.). All other chemicals were reagent grade or better.

Animals. Male Long-Evans rats (Harlan Sprague-Dawley, Madison, Wis.), which weighed 250-350 g, were used throughout these experiments. All animals were supplied food and water ad libitum and maintained on a 12 hour light/dark schedule in a temperature- and humidity-controlled environment. Animals were handled in accordance with the Guide for the Care and Use of Laboratory Animals as adopted and promulgated by the National Institutes of Health.

Methanol-intoxication Protocol. Animals were randomly assigned to one of four treatment groups: (1) Untreated control, (2) LED-treated control, (3) methanol-intoxicated and (4) LED-treated methanol-intoxicated rats. Rats were placed in a thermostatically controlled plexiglass chamber (22×55× 22 cm; maintained at 22-23° C.) and exposed to a mixture of $N_2O/O_2$ (1:1; flow rate 2 liters/min) for the duration of the experiment. $N_2O/O_2$ exposure produces a transient state of tetrahydrofolate deficiency in the rat resulting in formate accumulation following methanol administration (J. T. Eells, et al., supra, 2000). In the present studies, methanol (25% w/v methanol in saline) was administered (i.p.) to $N_2O/O_2$ treated rats at an initial dose of dose 4 g/kg, followed by supplemental doses of 1.5 g/kg at 24 and 48 hours. This methanol intoxication protocol has been shown to produce a state of prolonged formic acidemia with formate concentrations between 5-8 mM in methanol-intoxicated rats resulting in visual dysfunction (M. T. Seme, et al., supra, 1999; M. T. Seme, et al., supra, 2001). Moreover, similar concentrations of blood formate over similar time periods have been shown to produce ocular toxicity experimentally in monkeys and have been associated with visual toxicity in human methanol intoxication (J. T. Eells, supra, 1992; R. Kavet and K. Nauss, supra, 1990; S. O. Ingemansson, supra, 1983). Formate concentrations were determined from tail vein blood samples by fluorometric analysis as previously described (M. T. Seme, et al., supra, 1999; M. T. Seme, et al., supra, 2001; T. G. Murray, et al., 1991).

Light-Emitting Diode Treatment. GaAlAs light emitting diode (LED) arrays of 670 nm wavelength (LED bandwidth 25-30 nm at 50% power) were obtained from Quantum Devices, Inc. (Barneveld, Wis.). Rats were placed in a plexiglass restraint device (12.7×9×7.6 cm). The LED array was positioned directly over the animal at a distance of 1 inch, exposing the entire body. Treatment consisted of irradiation at 670 nm for 2 minutes and 24 seconds resulting in a power intensity of 28 $mW/cm^2$ and an energy density of 4 $joules/cm^2$ at 5, 25 and 50 hours after the initial dose of methanol. These stimulation parameters (670 nm at an energy density of 4 $J/cm^2$) had been demonstrated to be beneficial for wound healing, and to stimulate cellular proliferation and cytochrome oxidase activity in cultured visual neurons (H. T. Whelan, et al., supra, 2001; M. T. T. Wong-Riley, et al., supra, 2001).

ERG Procedures and Analyses. ERG experiments were performed as previously described (M. T. Seme, et al., supra, 1999; M. T. Seme, et al., supra, 2001). The light stimulation apparatus consisted of a three-beam optical system. All three beams were derived from tungsten-halide lamps (50 W, 12 V). Beam intensity was controlled by using neutral density step filters. ERG recordings were differentially amplified and computer-averaged. The amplified signal was processed through a two-stage active narrow bandpass filter (the half voltage of this filter was 0.2 times the center frequency). To ensure that any transients in the response that occur at the onset of the stimulus pulses were not included in the average, the initiation of signal averaging was delayed by a preset number of stimulus cycles (typically a minimum of 20). The resulting ERG is an extremely noise-free, single cycle, sinusoidal waveform. The averaged responses were measured (peak-to-trough amplitude) from a calibrated digital oscilloscope display.

Before ERG analysis, ophthalmoscopic examination confirmed that all eyes were free of lenticular opacities or other gross anomalies. Rats were anesthetized with thiobutabarbitol sodium salt (100 mg/kg, i.p.), positioned in a Kopf stereotaxic apparatus and placed on a heating pad to maintain core body temperature at 37° C. Atropine sulfate (0.05 mg/kg, s.q.) was administered to inhibit respiratory-tract secretions. The pupil of the eye to be tested was dilated by topical application of 1% atropine sulfate. Methylcellulose was topically applied as a lubricant and to enhance electrical conduction. A circular silver, wire recording electrode was positioned on the cornea, a reference electrode was placed above the eye, and a ground electrode was placed on the tongue. Recordings were obtained under ambient light conditions from cool white fluorescent room lights approximately 100 $cd/m^2$ at the rat's eye. Flickering stimuli (light/dark ratio=0.25:0.75) were presented. Responses to 60 successive flashes were averaged for each stimulus condition. At each test wavelength, a minimum of four stimulus intensities spaced at intervals of 0.3 log unit, were presented. The stimulus intensity yielding a 5-μV criterion response was determined by extrapolating between the two intensity points that bracketed the 5-μV response for each animal. All sensitivity measures were made in triplicate.

Two experimental protocols were used to evaluate retinal function. (J. F. Rizzo, supra, 1995)

15 Hz/510 nm ERG Response. ERGs were recorded in response to a 15-Hz flickering light at a wavelength of 510 nm over a 3-log unit range of light intensity. For these studies, the unattenuated stimulus (log relative retinal illumination=0) had an irradiance of 25 μW distributed over the 70° patch of illuminated retina. This can be calculated to produce retinal illumination equivalent to about $10^4$ scotopic trolands. These recording conditions disadvantage rods; however, since at least 97% of rat photoreceptors are rods and ERGs are recorded at luminance intensities ranging from $10^1$ to $10^4$ scotopic trolands, it is likely that the responses to the 15 Hz/510 nm light are drawn from both rods and medium wavelength cones (M-cones) (M. T. Seme, et al., supra, 1999; M. T. Seme, et al., supra, 2001; D. A. Fox and L. Katz, *Vision Res.* 32:249-255, 1992).

25 Hz/UV ERG Response. UV-sensitive cone responses were elicited by a 25-Hz flickering ultraviolet light (380-nm cut off) in the presence of an intense chromatic adapting light (445 μW) which eliminated responses mediated by rods and M-cones (G. Jacobs, et al., *Nature* 353:655-656, 1991). The 25-Hz/UV ERG responses were recorded over a 1.5-log unit range of light intensity. For these studies, the unattenuated stimulus (log relative retinal illumination=0) had an irradiance of 25 μW distributed over the 70° patch of illuminated retina. This can be calculated to produce retinal illumination equivalent to about $10^4$ scotopic trolands in the rat eye.

Histopathologic Analysis. Retinal tissue was prepared for histology as previously described (M. T. Seme, et al., supra, 1999; M. T. Seme, et al., supra, 2001). Thick sections (1μ) for light microscopy were stained with toluidine blue; thin sections for electron microscopy were stained for uranyl acetate-lead citrate (M. T. Seme, et al., supra, 1999; M. T. Seme, et al., supra, 2001).

Statistical Analysis. All values are expressed as means±SEM. A one-way ANOVA with Bonferroni's test was used to determine whether any significant differences existed among groups for blood formate concentrations. For ERG studies, a two-way ANOVA was performed. In all cases, the minimum level of significance was taken as P<0.05.

Results

Blood formate accumulation in methanol-intoxicated rats is not altered by 670 nm LED treatment. Formic acid is the toxic metabolite responsible for the retinal and optic nerve toxicity produced in methanol intoxication (G. Martin-Amat, et al., supra, 1977; J. T. Eells, supra, 1992; J. T. Eells, et al., supra, 2000; G. Martin-Amat, et al., supra, 1978). Linear increases in blood formate concentrations were observed in both methanol-intoxicated and LED-treated methanol-intoxicated rats during the 72-hour intoxication period (FIG. 1).

Referring to FIG. 1, photobiomodulation does not alter blood formate concentrations in methanol-intoxicated rats. Blood formate concentrations were determined before methanol administration and at 24 hour intervals after methanol administration for 72 hours. Shown are the mean values±SEM from six rats in each experimental group. Blood formate concentrations did not differ between the methanol-intoxicated and LED-treated, methanol-intoxicated groups (P>0.05).

In both treatment groups, blood formate concentrations increased tenfold from endogenous concentrations of 0.5-0.6 mM prior to methanol administration to nearly 6 mM following 72 hours of intoxication. The rate of formate accumulation and blood formate concentrations did not differ between the two treatment groups, indicating that LED treatment did not alter methanol or formate toxicokinetics. Similar increases in blood formate have been shown to disrupt retinal function in methanol intoxicated rats (M. T. Seme, et al., supra, 1999; M. T. Seme, et al., supra, 2001) and have been associated with visual toxicity in human methanol intoxication (J. T. Eells, supra, 1992; R. Kavet and K. Nauss, supra, 1990).

Methanol-induced retinal dysfunction is attenuated by 670-nm LED treatment. Following 72 hours of methanol intoxication, the function of rods and M-cones was assessed by recording the retinal response to a 15-Hz flickering light at wavelength of 510 nm (M. T. Seme, et al., supra, 1999; M. T. Seme, et al., supra, 2001).

Figure 2:
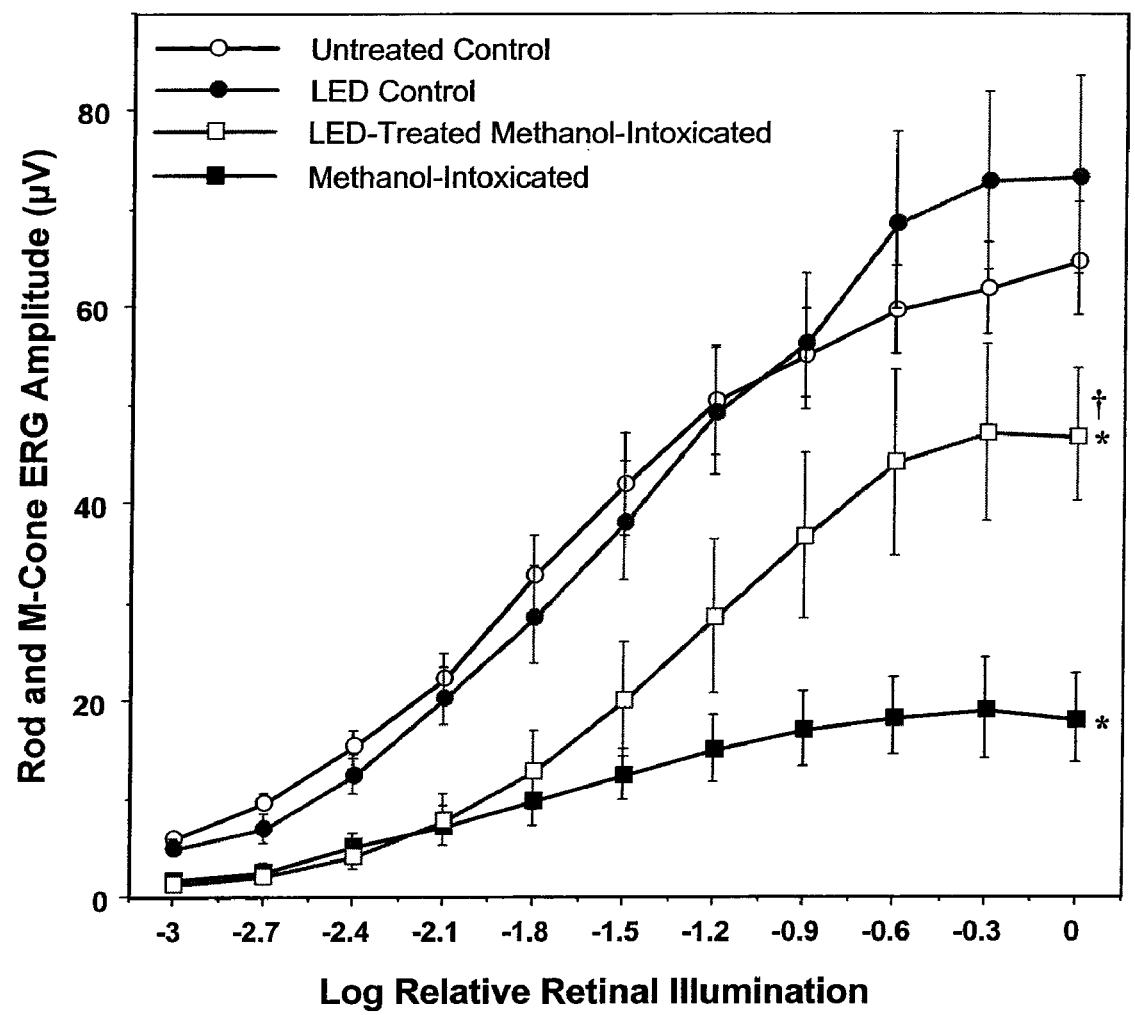
FIG. 2 is a graph of rod and M-cone ERG amplitude (μV) versus log relative retinal illumination.

Referring to FIG. 2, photobiomodulation improves rod and M-cone ERG response in methanol-intoxicated rats. Rod and M-cone (15 Hz/510 nm) ERG analysis was performed after 72 hours of methanol intoxication. Shown are the mean values±SEM from six rats in the untreated control, methanol-intoxicated, and LED-treated, methanol-intoxicated experimental groups and four rats from the LED control group. ERG responses in methanol-intoxicated and LED-treated, methanol-intoxicated rats were significantly lower than those measured in control rats (*, P<0.001). ERG responses in LED-treated, methanol-intoxicated rats were significantly greater than those measured in methanol-intoxicated rats (⊤, P<0.001).

In the untreated control group, 15-Hz/510-nm ERG amplitude increased linearly over the 3-log unit range of retinal illumination intensities, achieving a maximal amplitude of 65±5 µV at maximal retinal illumination (0 log relative retinal illumination (LRRI) equivalent to $10^4$ scotopic trolands). A similar ERG response profile was observed in LED-control animals. In both control groups a consistent 5-µV criterion threshold response was obtained at −3.0±0.1 LRRI. In agreement with our previous studies, methanol intoxication produced a profound decrease in retinal sensitivity to light coupled with an attenuation of maximal ERG response amplitude (M. T. Seme, et al., supra, 1999; M. T. Seme, et al., supra, 2001). The light intensity required to elicit a threshold (5 µV) 15-Hz/510-nm ERG response was increased by 0.6 log units to −2.4±0.1 LRRI in methanol-intoxicated rats relative to control animals. In addition, the amplitudes of the flicker ERG responses were significantly attenuated at all luminance intensities achieving a maximal amplitude of 18±5 µV, approximately 28% of the maximum control response. These changes are indicative of a severe deficit in retinal function and are consistent with formate-induced inhibition of photoreceptor oxidative metabolism (M. T. Seme, et al., supra, 1999; M. T. Seme, et al., supra, 2001; G. Jacobs, et al., supra, 1991; A. Koskelainen, et al, *Vision Res.* 34:983-994, 1994; O. Findl, et al., *Invest. Ophthalmol. Visual Sci.* 36:1019-1026, 1995). LED treatment significantly improved rod and M-cone mediated ERG responses in methanol intoxicated rats. At lower luminance intensities (<1.5 LRRI), LED treatment had no effect on ERG response; however, at luminance intensities >1.5 LRRI, ERG responses were significantly greater in LED-treated rats compared to methanol intoxicated animals. The maximal rod and M-cone in LED-treated rats was 47±8 µV, 72% of the maximal control response. These data are indicative of a partial recovery of rod and M-cone function by LED photobiomodulation in methanol-intoxicated rats.

The function of UV-sensitive cones was examined by recording the retinal response to a 25-Hz flickering ultraviolet light (380-nm cutoff) in the presence of an intense chromatic adapting light. These conditions have been shown to isolate the UV-cone response in the rat retina (G. Jacobs, et al., supra, 1991). The effects of methanol intoxication and LED light treatment on UV-cone ERG responses are shown in FIG. 3.

Figure 3:
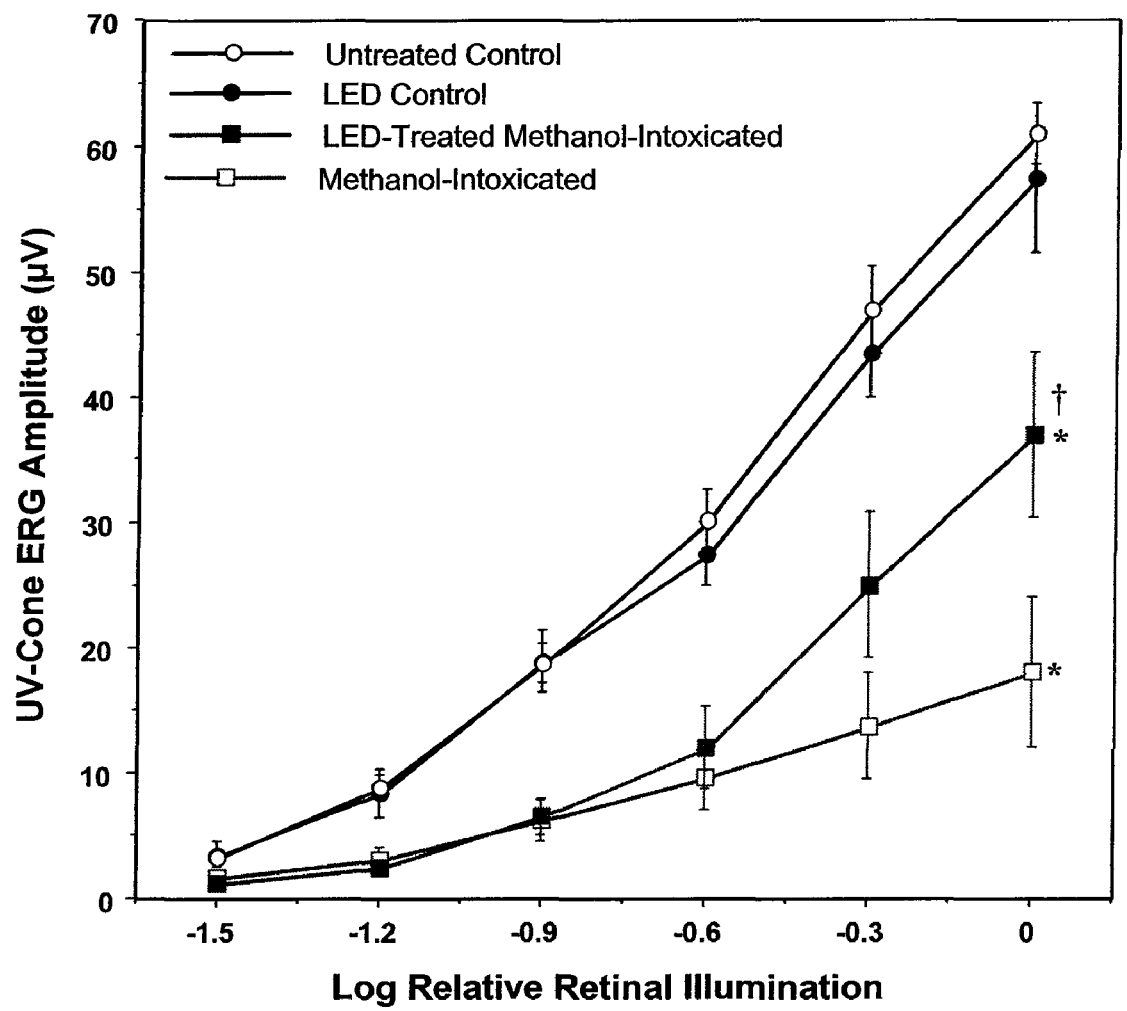
FIG. 3 is a graph of UV-cone ERG amplitude (μV) versus log relative retinal illumination.

Referring to FIG. 3, photobiomodulation improves UV-cone ERG response in methanol-intoxicated rats. UV-cone (25 Hz/380 nm) ERG analysis was performed after 72 hours of methanol intoxication. Shown are the mean values±SEM from six rats in the control, methanol-intoxicated, and LED-treated, methanol-intoxicated experimental groups and four rats from the LED control group. UV-cone ERG responses were recorded from the same animals in which the rod and M-cone responses were recorded. ERG responses in methanol-intoxicated and LED-treated, methanol-intoxicated rats were significantly lower than those measured in control rats (*, P<0.001). ERG responses in LED-treated, methanol-intoxicated rats were significantly greater than those measured in methanol-intoxicated rats (⊤, P<0.05).

In untreated control animals the UV-cone-mediated ERG amplitude increased linearly from a 5-µV threshold value (−1.4±0.03 LRRI) to a maximal value of 56±3 µV over the 1.5-log unit range of retinal illumination used in these studies. LED-treated control animals exhibited a similar ERG response profile to that observed in untreated control animals. In methanol-intoxicated rats, the UV-cone ERG response was profoundly attenuated consistent with our previous studies (M. T. Seme, et al., supra, 1999; M. T. Seme, et al., supra, 2001). The light intensity required to elicit a 5-µV response was increased by 0.5 log units to 0.9±0.08 LRRI in intoxicated animals, and the maximal response amplitude was reduced to 18±6 µV, 30% of the maximum control response. Similar to what we observed in the rod and M-cone ERG studies, LED treatment had no effect on UV-cone ERG response at lower luminance intensities, but significantly improved ERG response at higher luminance intensities. The maximal UV-cone ERG response in LED-treated rats was 37±7 µV, 61% of the control response indicative of a partial recovery of UV-cone function by LED photobiomodulation.

Figure 4:
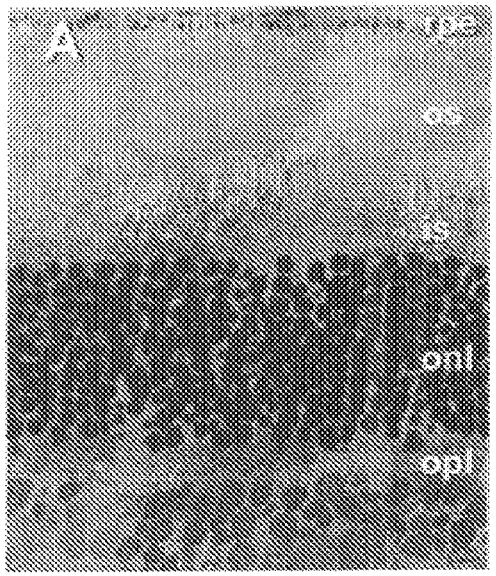
FIG. 4(A-D) is a set of micrographs illustrating outer retinal morphology in representative untreated control (FIG. 4A), LED control (FIG. 4B), methanol-intoxicated (FIG. 4C), and LED-treated, methanol-intoxicated (FIG. 4D) retinas.
Figure 4:
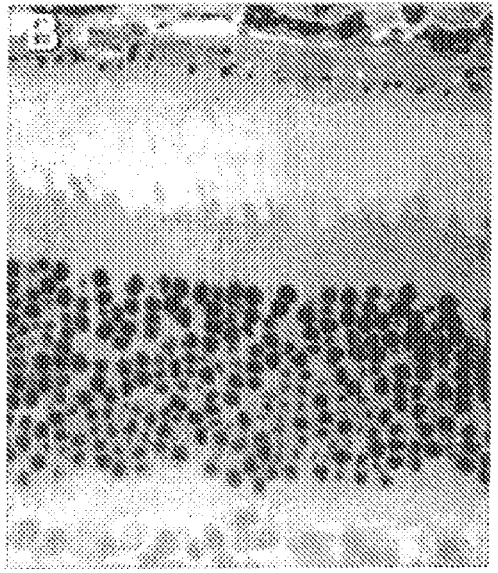
Figure 4:
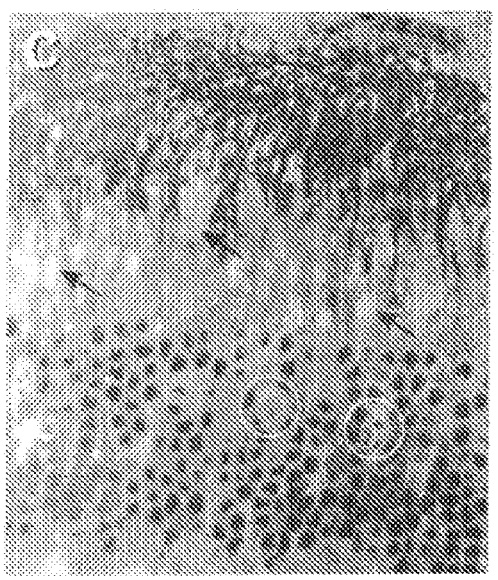
Figure 4:
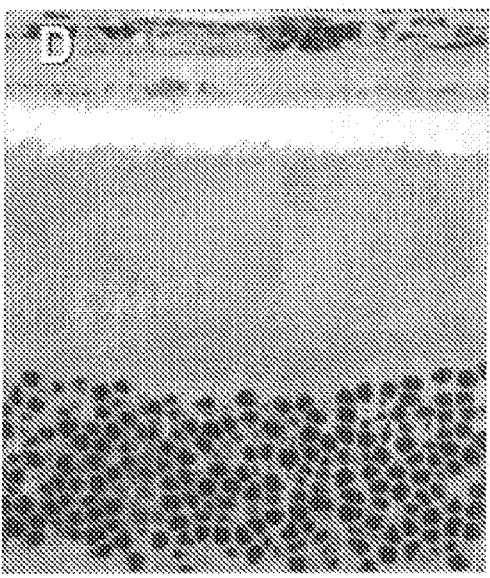

Methanol-induced retinal histopathology is prevented by 670 nm LED treatment. The architecture of the retina in methanol-intoxicated and LED-treated methanol intoxicated rats was evaluated by light and electron microscopy. These studies focused on the outer retina at the level of the photoreceptors based on our previous findings of outer retinal pathology and photoreceptor mitochondrial disruption following methanol intoxication (M. T. Seme, et al., supra, 1999; M. T. Seme, et al., supra, 2001; T. G. Murray, et al., supra, 1991). FIG. 4 illustrates outer retinal morphology in representative untreated control (FIG. 4A), LED control (FIG. 4B), methanol intoxicated (FIG. 4C), and LED-treated methanol intoxicated (FIG. 4D) retinas.

Referring to FIG. 4, photobiomodulation protects retinal morphology in methanol-intoxicated rats. Outer retinal morphology in representative untreated control (A), LED control (B), methanol-intoxicated (C), and LED-treated, methanol-intoxicated (D) rats. Sections were taken from the posterior pole of the retina within two disk diameters of the optic nerve in any direction. (Toluidine blue, ×450.) (A) rpe, retinal pigment epithelium; os, photoreceptor outer segments; is, photoreceptor inner segments; onl, outer nuclear layer; opl, outer plexiform layer; ipl, inner plexiform layer. (B) The arrows indicate enlargement and swelling of the photoreceptor inner segments, and the circles indicate the fragmented appearance of photoreceptor nuclei. No histopathologic changes were apparent at the light microscopic level in the LED control or LED-treated, methanol-intoxicated groups.

Pronounced histopathologic changes were apparent in the outer retina of methanol-intoxicated rats (FIG. 4C), including evidence of retinal edema, swelling of photoreceptor inner segments, and morphologic changes in photoreceptor nuclei. Retinal edema was evidenced by the spacing between the photoreceptor inner segments, and by the spacing of the nuclei in the outer nuclear layer. Photoreceptor inner segments were profoundly swollen and enlarged, and photoreceptor nuclei in the outer nuclear layer appeared fragmented with irregularly stained chromatin. In contrast, LED-treated methanol-intoxicated animals (FIG. 4D) exhibited retinal morphology which was indistinguishable from untreated control rats (FIG. 4A) and LED treated control rats (FIG. 4B). In these animals outer retinal morphology was characterized by ordered photoreceptor inner segments with no evidence of vacuolization or swelling and the outer nuclear layer was compact with round and well-defined nuclei. The lack of retinal histopathology in LED-treated methanol intoxicated rats provides additional evidence of the retinoprotective actions of 670-nm LED treatment.

Figure 5:
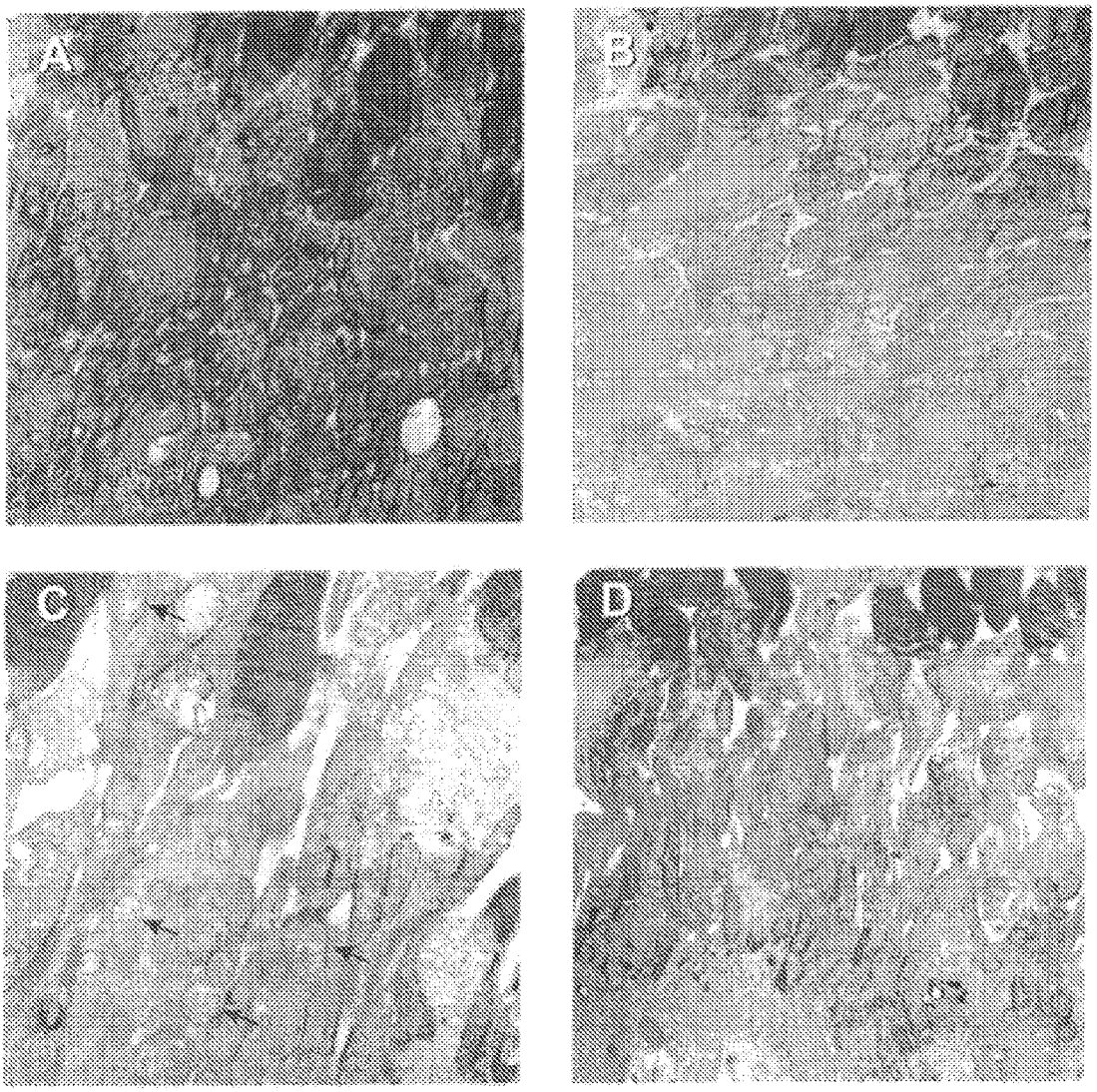
FIG. 5(A-D) is a set of electron micrographs of the rod inner segment region in representative untreated control (FIG. 5A) LED control, (FIG. 5B) methanol-intoxicated, (FIG. 5C) and LED-treated, methanol-intoxicated (FIG. 5D) rats.

The most obvious ultrastructural change observed in the outer retina of methanol-intoxicated rats was swelling and disruption of mitochondria in the inner segments of the photoreceptors. Referring to FIG. 5, photobiomodulation protects photoreceptor ultrastructure in methanol-intoxicated rats. Electron micrographs of the rod inner segment region in representative untreated control (A), LED control (B), methanol-intoxicated (C), and LED-treated, methanol-intoxicated (D) rats. The arrows indicate abnormal mitochondrial morphology in photoreceptor inner segments. Photoreceptor mitochondria from LED control or LED-treated, methanol-intoxicated rats exhibited normal morphology with well-defined cristae, (Magnifications: ×5,000).

Some mitochondria were swollen and contained expanded cristae; other mitochondria were disrupted and showed no evidence of cristae (FIG. 5C). In contrast, mitochondria in the photoreceptor inner segments from LED-treated, methanol-intoxicated rats (FIG. 5D) exhibited normal morphology with well-defined cristae similar to inner segment mitochondrial morphology in untreated control rats (FIG. 5A) and LED-treated control rats (FIG. 5B). The absence of mitochondrial damage in photoreceptors of LED-treated methanol-intoxicated rats strongly supports our hypothesis that 670-nm LED treatment preserved mitochondrial function.

Discussion

Low-energy photon irradiation by light in the far-red to near-IR spectral range (630-1000 nm) using low-energy lasers or LED arrays has been found to modulate various biological processes in cell culture and animal models (M. J. Conlan, et al., supra, 1996; W. Yu, et al., supra, 1997; A. P. Sommer, et al., supra, 2001; T. Karu, supra, 1999). This phenomenon of photobiomodulation has been applied clinically in the treatment soft tissue injuries and to accelerate wound healing (H. T. Whelan, et al., supra, 2001; M. J. Conlan, et al., supra, 1996). The mechanism of photobiomodulation by red to near-IR light at the cellular level has been ascribed to the activation of mitochondrial respiratory chain components, resulting in initiation of a signaling cascade which promotes cellular proliferation and cytoprotecton (T. Karu, supra, 1999; N. Grossman, et al., supra, 1998; M. T. T. Wong-Riley, et al., supra, 2001). A comparison of the action spectrum for cellular proliferation after photoirradiation with the absorption spectrum of potential photoacceptors lead Karu (T. Karu, supra, 1999) to suggest that cytochrome oxidase is a primary photoreceptor of light in the red to near-IR region of the spectrum.

Recent studies conducted in primary neuronal cultures by our research group have shown that 670-nm LED photobiomodulation reversed the reduction in cytochrome oxidase activity produced by the blockade of voltage-dependent sodium channel function by tetrodotoxin and up-regulated cytochrome oxidase activity in normal neurons (M. T. T. Wong-Riley, et al., supra, 2001). The present studies extended these investigations to an in vivo system to determine if 670-nm LED photobiomodulation would improve retinal function in an animal model of formate-induced mitochondrial dysfunction. Results of this study demonstrate the therapeutic benefit of photobiomodulation in the survival and functional recovery of the retina in vivo after acute injury by the mitochondrial toxin, formic acid generated in the course of methanol intoxication. We provide in vivo evidence that three brief post-methanol-intoxication treatments with 670-nm LED photoirradiation promotes the recovery of retinal function in rod and cone pathways and protects the retina from the histopathologic changes induced by methanol-derived formate. These findings provide a link between the actions of red to near-IR light on mitochondrial oxidative metabolism in vitro and retinoprotection in vivo.

Low-energy laser irradiation has documented benefits in promoting the healing of hypoxic, ischemic, and infected wounds (H. T. Whelan, et al., supra, 2001; M. J. Conlan, et al., supra, 1996). However, lasers have limitations in beam width, wavelength capabilities, and size of wounds that can be treated (H. T. Whelan, et al., supra, 2001). Heat generated from the laser light can damage biological tissue, and the concentrated beam of laser light may accidentally damage the eye. LED arrays were developed for National Aeronautics and Space Administration manned space flight experiments. In comparison to lasers, the patented LED technology generates negligible amounts of heat, is clinically proven to be safe, and has achieved non-significant risk status for human trials by the Food and Drug Administration (H. T. Whelan, et al., supra, 2001). The wavelength, power, and energy parameters used in the present study are based on their beneficial effects for wound healing in humans (H. T. Whelan, et al., supra, 2001) and stimulation of CO activity in cultured neuronal cells (M. T. T. Wong-Riley, et al., supra, 2001).

The retinoprotective actions of 670-nm LED treatment in the present study are consistent with the actions of formate as a mitochondrial toxin and the actions of 670-nm light on cytochrome oxidase activity. Formate has been shown to reversibly inhibit cytochrome oxidase activity with an apparent inhibition constant between 5 and 30 mM (P. Nicholls, supra, 1975; P. Nicholls, supra, 1976). Blood formate concentrations in methanol-intoxicated rats in the present study fall within this range and retinal formate concentrations closely parallel blood formate concentrations (J. T. Eells, et al., supra, 2000). The functional and morphologic alterations produced in the retina by methanol-derived formate are indicative of formate-induced inhibition of photoreceptor mitochondrial energy metabolism. Photoreceptors are the most metabolically active cells in the body, and the energy required for phototransduction is derived primarily from oxidative metabolism (A. Ames, III, et al., *J. Neurosci.* 12:840-853, 1992; A. Ames, III, *Can. J. Physiol. Pharmacol.* 70:S158-S164, 1992). The loss of retinal sensitivity to light and attenuation of ERG response in methanol-intoxicated rats are indicative of formate-induced inhibition of photoreceptor oxidative energy metabolism and are similar to the actions of other metabolic poisons in the retina (M. T. Seme, et al., supra, 1999; A. Koskelainen, et al., supra, 1994; O. Findl, et al., supra, 1995). The observed mitochondrial swelling and disruption in the photoreceptor inner segments in methanol-intoxicated rats are consistent with a disruption of ionic homeostasis secondary to inhibition of cytochrome oxidase. Moreover, similar morphologic alterations have been reported in the retinas of patients with mitochondrial diseases that inhibit electron transport (P. A. McKelvie, et al., *J. Neurol. Sci.* 102:51-60, 1991; L. M. Rapp, et al., *Invest. Ophthalmol. Visual Sci.* 31:1186-1190, 1990; P. Runge, et al., *Br. J. Ophthalmol.* 70:782-796, 1986).

In the present study, the increase in ERG response and the lack of damage to photoreceptor mitochondria in LED-treated, methanol-intoxicated rats are indicative of a biostimulatory effect of 670-nm light on photoreceptor bioenergetics. A growing body of evidence suggests that cytochrome oxidase is a key photoacceptor of light in the far red to near infrared spectral range (T. Karu, supra, 1999; W. Yu, et al., supra, 1997; S. Passarella, et al., *FEBS Lett.* 175:95-99, 1984; D. Pastore, et al., *Int. J. Radiat. Biol.* 76:863-870, 2000). Cytochrome oxidase is an integral membrane protein which contains four redox active metal centers and has a strong absorbance in the far-red to near-IR spectral range detectable in vivo by near-IR spectroscopy (C. E. Cooper and R. Springett, *Philos. Trans. R. Soc. London B* 352:9-676, 1977; B. Beauvoit, et al., *Anal. Biochem.* 226:167-174, 1995; B. Beauvoit, et al., *Biophys. J.* 67:2501-2510, 1994). Moreover, 660-680 nm irradiation has been shown to increase electron transfer in purified cytochrome oxidase (D. Pastore, et al., supra, 2000), increase mitochondrial respiration and ATP synthesis in isolated mitochondria (S. Passarella, et al., supra, 1984), and to up regulate cytochrome oxidase activity in cultured neuronal cells (M. T. T. Wong-Riley, et al., supra, 2001). An up-regulation of retinal cytochrome oxidase by LED treatment would effectively counteract the inhibitory actions of formate on retinal oxidative metabolism, thus improving retinal function. Although retinal function was improved in LED-treated rats, it was not restored to control response levels. At lower luminance intensities, LED treatment did not improve the ERG response in methanol-intoxicated rats suggesting that the rate of activation of some components of phototransduction activation remained compromised by formate. Because the rate of activation of phototransduction depends on an adequate supply of GTP and ATP (G. Jacobs, et al., supra, 1991; A. Koskelainen, et al., supra, 1994; O. Findl, et al., supra, 1995), it is possible that the formate-induced metabolic inhibition is only partly attenuated by our LED treatment protocol.

The prolonged effect of three brief LED treatments in mediating the retinoprotective actions in methanol intoxication suggests that 670-nm LED photostimulation induces a cascade of signaling events initiated by the initial absorption of light by cytochrome oxidase. These signaling events may include the activation of immediate early genes, transcription factors, cytochrome oxidase subunit gene expression, and a host of other enzymes and pathways related to increased oxidative metabolism (T. Karu, supra, 1999; M. T. T. Wong-Riley, et al., supra, 2001; C. Zhang and M. Wong-Riley, *Eur. J. Neurosci.* 12:1013-1023, 2000). In addition to increased oxidative metabolism, red to near-IR light stimulation of mitochondrial electron transfer is also known to increase the generation of reactive oxygen species (T. Karu, supra, 1999). These mitochondrially generated reactive oxygen species may function as signaling molecules to provide communication between mitochondria and the cytosol and nucleus and thus play an important signaling role in the activation of retinoprotective processes following LED treatment (S. Nemoto, et al., *Mol. Cell. Biol.* 20:7311-7318, 2000).

The results of this study demonstrate that photobiomodulation with red to near-IR light augments recovery pathways promoting neuronal viability and restoring neuronal function following injury. Importantly, there was no evidence of damage to the normal retina following 670-nm LED treatment. Based on these findings, we propose that photobiomodulation represents an innovative and novel therapeutic approach for the treatment of retinal injury, as well as the treatment of retinal diseases including age-related macular degeneration, glaucoma, diabetic retinopathy and Leber's hereditary optic neuropathy.

Example 2

Animal Model of Retinal Protection

Methanol intoxication produces toxic injury to the retina and optic nerve frequently resulting in blindness. The toxic metabolite in methanol intoxication is formic acid, a mitochondrial toxin known to inhibit the essential mitochondrial enzyme, cytochrome oxidase. The Eells' laboratory has developed a rodent model of methanol toxicity which replicates the metabolic and retinotoxic manifestations of human methanol toxicity. This animal model also manifests many features associated with retinal aging and many clinically important retinal and optic nerve diseases and thus serves as an excellent experimental model for the investigation of treatments for retinal and optic nerve disease.

Studies were undertaken to determine if exposure to monochromatic 670 nm radiation from light-emitting diode (LED) arrays would protect the retina against the toxic actions of methanol-derived formic acid in this animal model of ocular disease. Methanol-intoxicated and non-intoxicated control rats were placed in a plexiglass restraint device (12.7×9×7.6 cm). The LED array was positioned directly over the animal at a distance of 2.5 cm. Treatment consisted of irradiation at 670 nm for 2 min and 24 sec resulting in a power intensity of 28 mW/cm$^2$ and an energy density of 4 joules/cm$^2$. NIR-LED treatments were administered 5, 25 and 50 hours after the initial dose of methanol. These stimulation parameters (670 nm at an energy density of 4 J/cm$^2$) have been demonstrated to be beneficial for wound healing, and to stimulate cellular proliferation and cytochrome oxidase activity in cultured visual neurons.

Figure 6A:
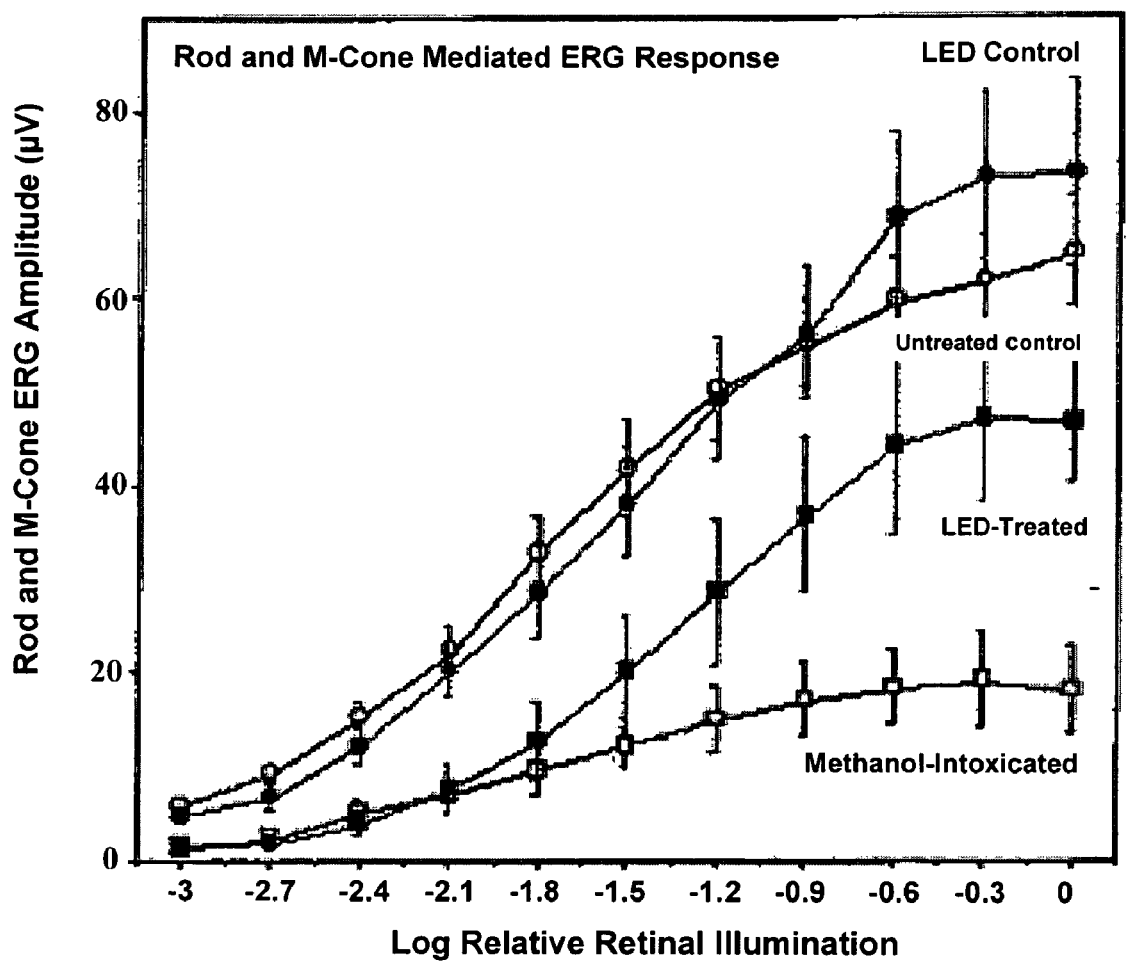
FIG. 6A is a graph of rod and M-cone ERG amplitude versus log relative retinal illumination.
Figure 6B:
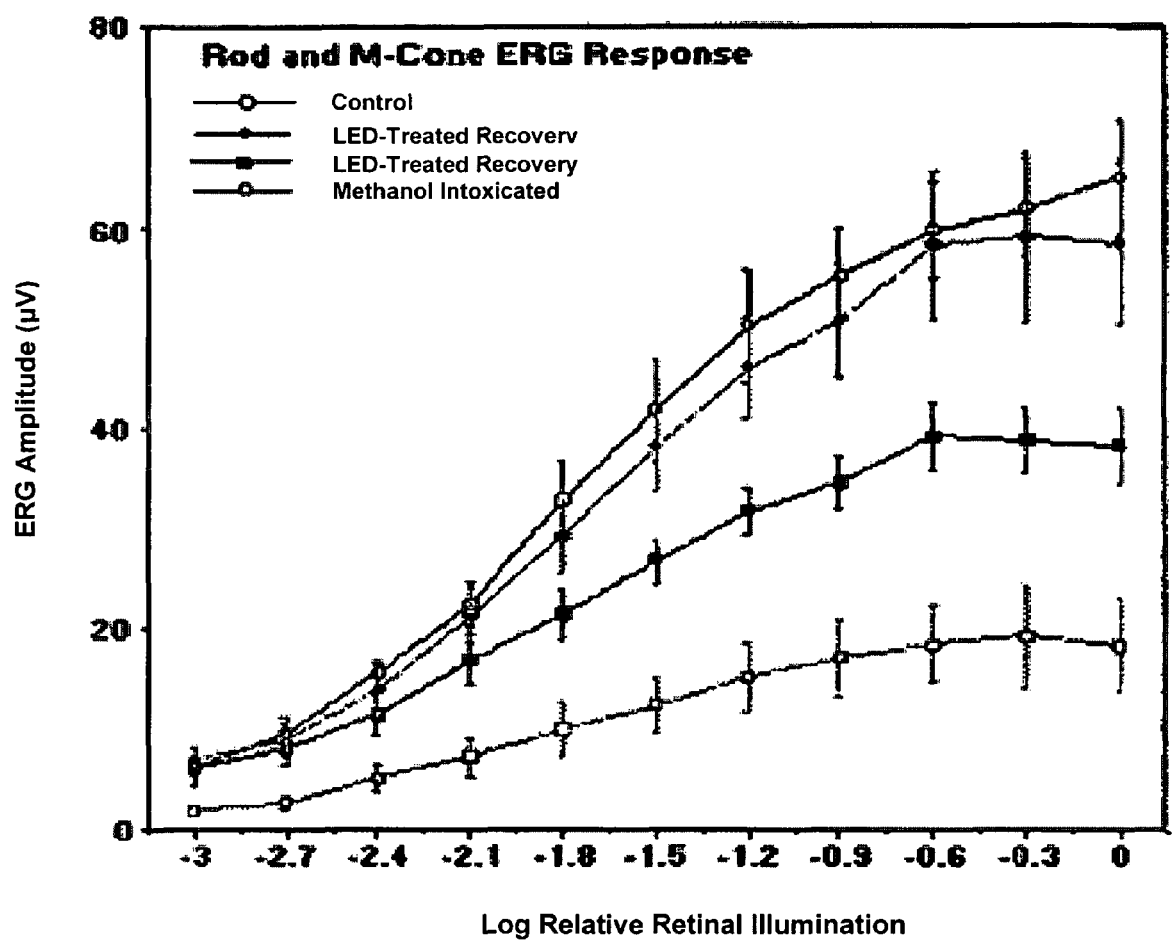
FIG. 6B is a graph of ERG amplitude versus log relative retinal illumination.

The electroretinogram (ERG) which measures the response of the retina to flickering light stimulation was used as a sensitive and clinically relevant indicator of retinal function. NIR-LED treated animals exhibited a dramatic improvement in retinal function measured by the ERG (FIG. 6) and NIR-LED treatment also protected the retina from the histopathologic damage induced by methanol-derived formate. These findings provide a link between the actions of monochromatic red to near infrared light on mitochondrial oxidative metabolism in vitro and retinoprotection in vivo.

Example 3

Nonhuman Primate Model of Retinal Protection

Figure 7:
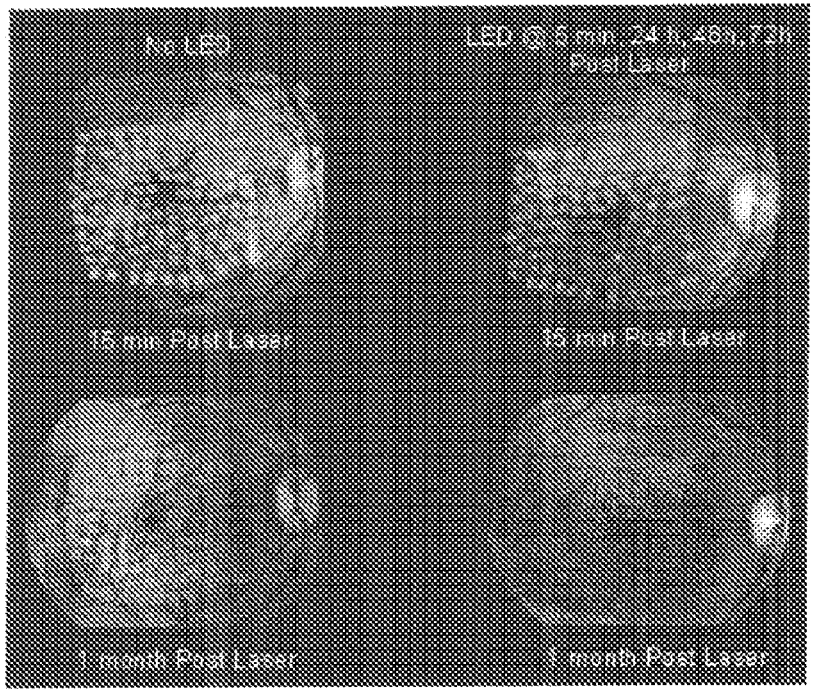
FIGS. 7A and B describes NIR LED treatment as improving healing following laser-induced retinal injury.
FIG. 7B is a bar graph of severity of burn (spot persistence) versus treatment.
Figure 7B:
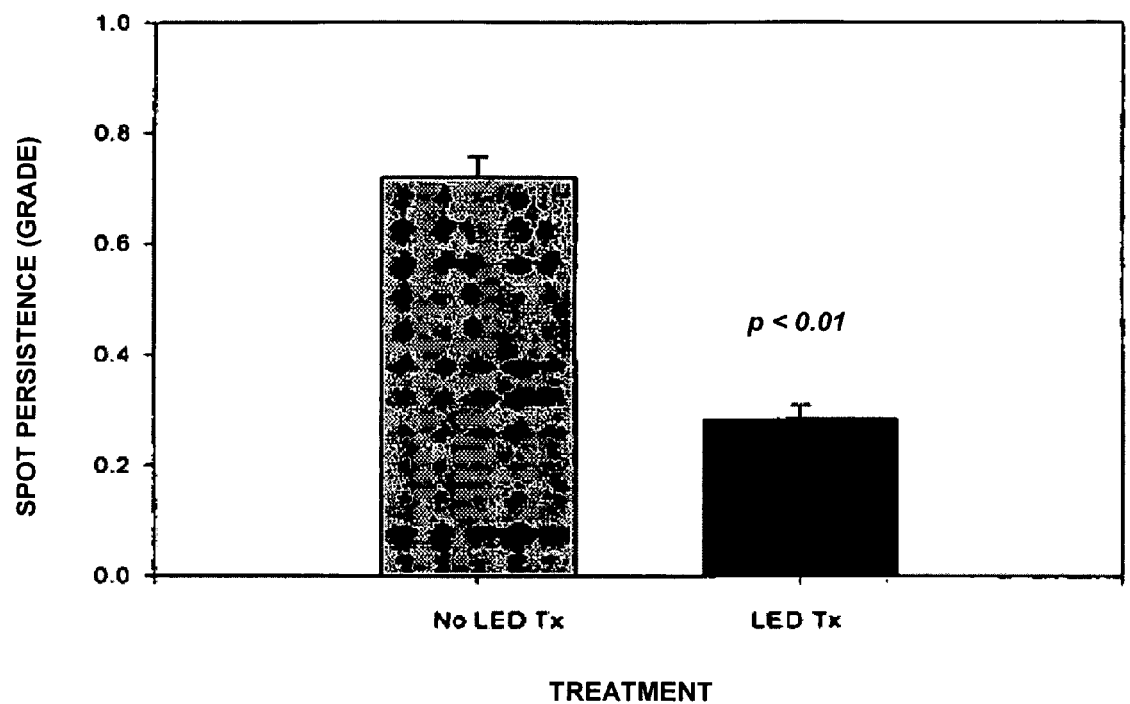
Figure 8:
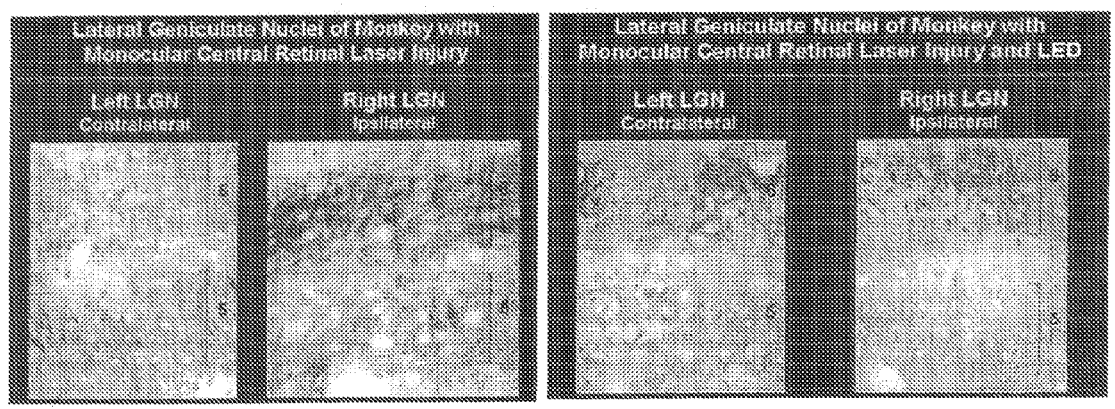
FIG. 8 describes NIR LED treatment as improving visual function.
Figure 8B:
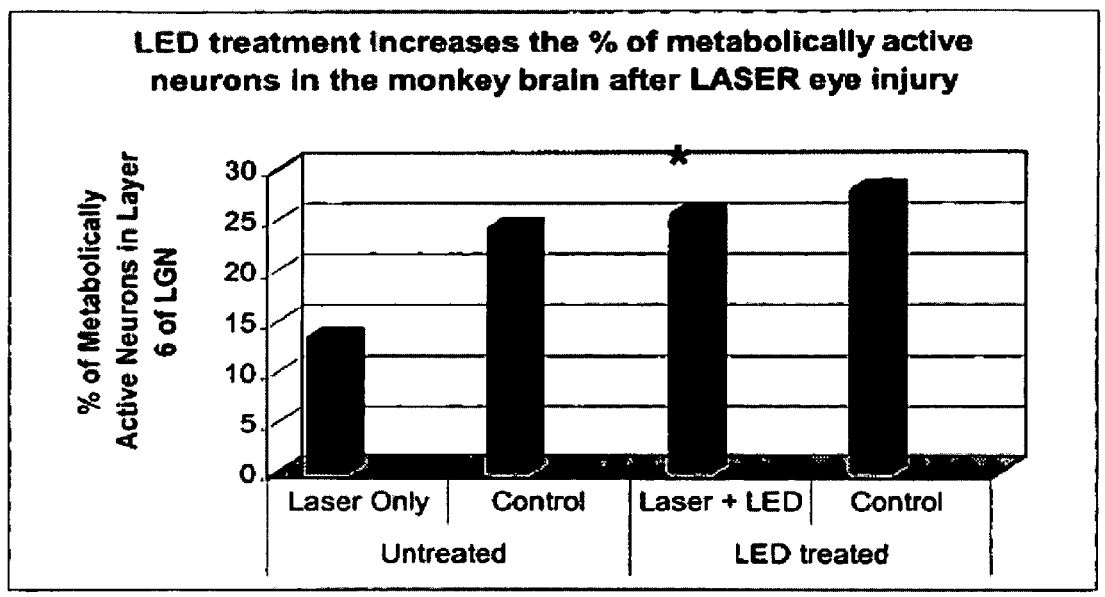
FIG. 8B is a bar graph of untreated and LED-treated subjects versus percentage of metabolically active neurons in layer 6 of LGN.

We have initiated studies of laser retinal injury in a nonhuman primate model. To date, we have performed two experiments using this animal model. In each experiment one monkey was lased without LED treatment and one lased with LED treatment (670 nm, 4 J/cm$^2$). A laser grid (128 spots delivered to the macula and perimacula) was created in the central retina of right eye of each animal. This grid consisted of grade I and II burns, photocoagulating the photoreceptors and outer nuclear layer of the retina. Multifocal ERG was performed to assess the functional state of the retina. In the first experiment, the LED-treated monkey was treated at 1, 24, 72 and 96 hours post injury. ERG amplitude in both LED treated and untreated monkeys was temporarily increased shortly after laser injury and this increase was greater in the LED-treated monkey. Assessment of the severity of the laser burn in LED treated and untreated animal demonstrated a greater that 50% improvement in the degree of retinal healing at 1 month post-laser in the LED-treated monkey (FIG. 7). In addition, the thickness of the retina measured at the fovea by optical coherence tomography did not differ from the pre-laser thickness in the LED-treated animal whereas it was 50% thinner in the untreated animal. Importantly, LED treatment prevented the loss of cytochrome oxidase staining (FIG. 8) in the lateral geniculate nucleus clearly showing that the brain was responding to visual input from the "healed" retina in the LED-treated animal much more effectively than in the untreated animal.

Figure 9:
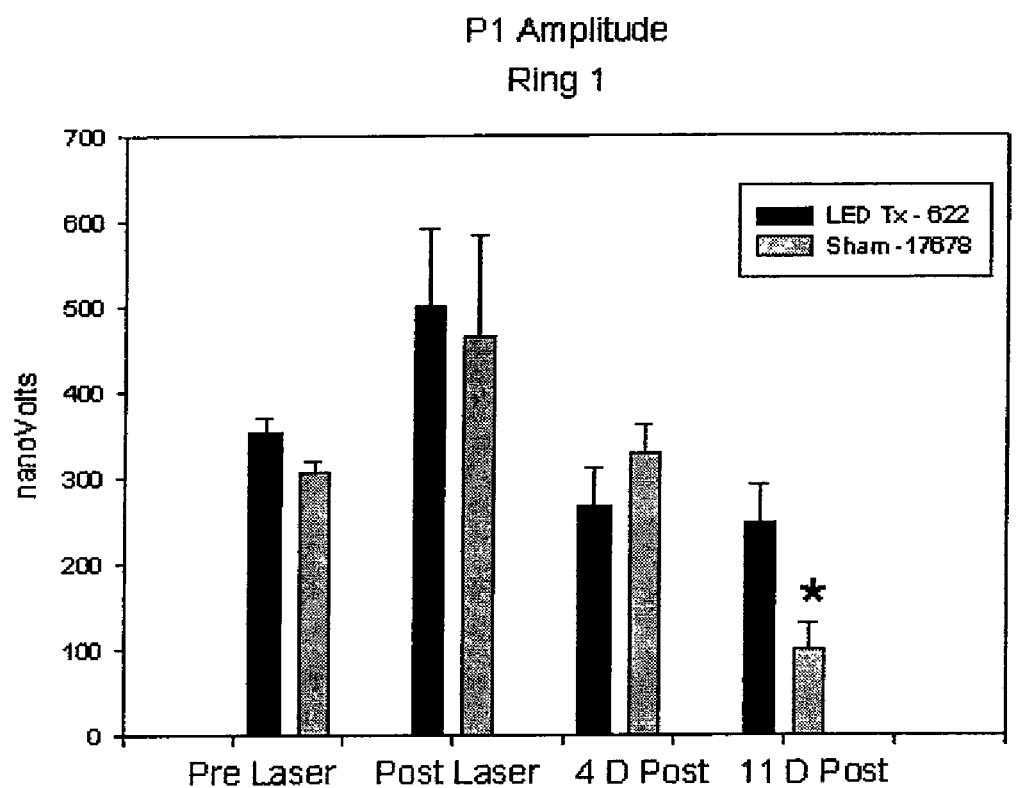
FIG. 9 describes NIR-LED treatment as improving retinal function.

In the second study, the LED-treated animal was treated once per day for 11 days and mfERG recordings were recorded (FIG. 9). Again, shortly after laser injury, the ERG amplitude was temporarily increased in both LED treated and untreated animals. However, in this experiment the increases were comparable. At 4 days post laser injury, the mfERG responses in LED treated and untreated animals had decreased to pre-laser amplitudes. However, by day 11 post laser, the mfERG response in the LED treated monkey was more than 50% greater than that measured in the untreated (sham) monkey. In both experiments, these preliminary findings are indicative of improved retinal healing and visual cortical function following LED treatment in laser injured primate model.

Example 4

Effect of NIR-LED Treatment in Leber's Hereditary Optic Neuropathy

The effect of NIR-LED treatment was investigated in the treatment of Leber's Hereditary Optic Neuropathy (LHON). LHON is a disease caused by a mitochondrial mutation (the most common mutation is in position 11778 of the mitochondrial genome) which results in defective mitochondrial energy production and causes blindness in early adulthood.

NIR-LED treatment was investigated in 6 affected (blind) 11778 LHON mutation carriers in Colatina, Brazil according to the protocol approved by the Institutional Review Board of San Paolo Federal University. Each subject exhibited a profound deficit in central vision. Baseline values for NSE, Humphrey 60° visual fields and nerve fiber analysis were obtained prior to LED treatment. LED treatment consisted of irradiation at 670 nm for 80 seconds delivered to each eye producing an estimated energy density of 4 joules/cm$^2$ at the optic nerve head. LED treatment was administered once per day for 3 days using handheld LED arrays (Quantum Devices, Barneveld, Wis.) positioned 2.5 cm from each closed eye. Treatment response was assessed 1 day following the third LED treatment (day 4) and again on day 10. Two of the NIR-LED-treated subjects reported a transient improvement in color vision and visual acuity lasting approximately one day. NSE concentrations in these two subjects increased dramatically (from a pre-exposure level of 0.9 µg/L to 7.6 µg/L in one subject and 2.2 µg/L to 5.3 µg/L in the other) in contrast to smaller increases or decreases in NSE measured in the other four subjects. Peripheral visual fields showed distinct improvement in 4 of the 6 patients by 10 days post treatment. No change was observed in nerve fiber layer measurements. No detrimental effects of NIR-LED treatment were reported by study subjects and no adverse effects were observed in visual function tests. The findings of this pilot study confirm and extend previous studies which have reported that NIR-LED exposure at energy densities up to 300 joules/cm$^2$ produces no detrimental effects on the retina and optic nerve. The studies further demonstrate that NIR-LED treatment exerts a beneficial effect in LHON.

We claim:

1. A method of treating visual system disease or injury, comprising the steps of
    a) exposing a component of a patient's visual system to light treatment in the absence of an exogenous photosensitizer, wherein the light treatment is characterized by a wavelength of 630-1000 nm and power intensity between 10-90 mW/cm$^2$, and
    b) performing one or more tests measuring visual function, wherein the test results indicate an increase in metabolically active neurons.

2. The method of claim 1 wherein the wavelength is selected from the group consisting of 670 nm, 830 nm and 880 nm.

3. The method of claim 1 wherein the wavelength is between 670-900 nm.

4. The method of claim 1 wherein the light treatment is characterized by an energy density of between 0.5-20 J/cm$^2$.

5. The method of claim 4 when the energy density is between 2-10 j/cm$^2$.

6. The method of claim 1 wherein the patient is exposed to light treatment multiple times.

7. The method of claim 6 wherein the exposure is at least 3 times.

8. The method of claim 6 wherein the patient is exposed to light treatment at intervals of 24 hours.

9. The method of claim 1 wherein the component of the visual system comprises the patient's retina.

10. The method of claim 1 wherein the component of the visual system is selected from the group consisting of cornea and optic nerve.

11. The method of claim 1 wherein the retinal function is evaluated.

12. The method of claim 1 wherein the light is supplied by an LED device.

13. The method of claim 1 wherein the power intensity is between 25-50 mW/cm$^2$.

14. A method of treating visual system disease or injury, comprising the steps of
    a) exposing a component of a patient's visual system to light treatment in the absence of an exogenous photosensitizer, wherein the light treatment is characterized by wavelength of 630-1000 nm and power intensity between 10-90 mW/cm$^2$, and
    b) performing electroretinography (ERG) to observe restoration or protection of visual function, wherein rod and cone ERG amplitude has increased relative to tissue that hasn't been exposed to the light treatment.

15. The method of claim 14 wherein the light treatment is applied for a time of 1-3 minutes.

16. The method of claim 14 wherein the light is supplied by an LED device.

17. The method of claim 1 wherein the light treatment is applied for a time of 1-3 minutes.

18. The method of claim 1 wherein the light treatment is applied at least 2-3 times a day.

19. The method of claim 1 wherein the patient is a human.

* * * * *

UNITED STATES PATENT AND TRADEMARK OFFICE
CERTIFICATE OF CORRECTION

PATENT NO. : 7,744,590 B2
APPLICATION NO. : 12/056458
DATED : June 29, 2010
INVENTOR(S) : Janis T. Eells et al.

It is certified that error appears in the above-identified patent and that said Letters Patent is hereby corrected as shown below:

Column 8, line 35 "eve" should be -- eye --

Signed and Sealed this

Thirty-first Day of August, 2010

David J. Kappos
*Director of the United States Patent and Trademark Office*